United States Patent
Pauser et al.

(10) Patent No.: US 10,478,852 B2
(45) Date of Patent: Nov. 19, 2019

(54) DEVICE FOR DISPENSING A MATERIAL

(71) Applicant: 3M INNOVATIVE PROPERTIES COMPANY, St. Paul, MN (US)

(72) Inventors: Helmut Pauser, Diessen (DE); Marc Peuker, Schoendorf (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/119,300

(22) PCT Filed: Feb. 25, 2015

(86) PCT No.: PCT/US2015/017438
§ 371 (c)(1),
(2) Date: Aug. 16, 2016

(87) PCT Pub. No.: WO2015/130739
PCT Pub. Date: Sep. 3, 2015

(65) Prior Publication Data
US 2017/0050210 A1 Feb. 23, 2017

(30) Foreign Application Priority Data
Feb. 26, 2014 (EP) .................................. 14156858

(51) Int. Cl.
*B05C 17/005* (2006.01)
*B05C 17/01* (2006.01)
*A61C 5/62* (2017.01)

(52) U.S. Cl.
CPC .......... *B05C 17/00576* (2013.01); *A61C 5/62* (2017.02); *B05C 17/00593* (2013.01); *B05C 17/0133* (2013.01)

(58) Field of Classification Search
CPC .......... B05C 17/00576; B05C 17/0133; B05C 17/00593; A61C 5/062; A61C 5/62; A45D 40/04; A61M 5/31515
(Continued)

(56) References Cited

U.S. PATENT DOCUMENTS 3,212,685 A * 10/1965 Swan ...................... A61M 3/00
222/386
4,312,343 A * 1/1982 LeVeen ............. A61M 5/31586
604/211
(Continued)

FOREIGN PATENT DOCUMENTS

WO   WO 2006-108085   10/2006

OTHER PUBLICATIONS

International Search Report for PCT International Application No. PCT/US2015/017438, dated Jun. 22, 2015, 5 pages.

*Primary Examiner* — Paul R Durand
*Assistant Examiner* — Robert K Nichols, II
(74) *Attorney, Agent, or Firm* — 3M Innovative Properties Compa

(57) ABSTRACT

A device for dispensing a material has a container for holding the material, a piston movably arranged within the container and a spindle in cooperation with the piston. The device is configured such that the spindle and the container are rotatable relative to each other to move the piston for dispensing the material. The piston and the spindle are adapted to anti-twist lock against each other in a first axial position of the piston relative to spindle. And in a second axial position of the piston relative to spindle the anti-twist lock between the piston and the spindle is suspended. The device helps minimizing any residual dental material upon attempting to empty the device.

9 Claims, 3 Drawing Sheets

(58) Field of Classification Search
USPC .......................................................... 222/390
See application file for complete search history.

(56) References Cited

U.S. PATENT DOCUMENTS

| | | | |
|---|---|---|---|
| 4,479,781 | A | 10/1984 | Herold |
| 5,591,027 | A * | 1/1997 | M uhlbauer ........... A61C 19/10 |
| | | | 433/90 |
| D419,236 | S | 1/2000 | Carlson |
| 6,089,774 | A | 7/2000 | Franken |
| 6,436,075 | B1 * | 8/2002 | Liao .................... A61M 5/3205 |
| | | | 604/181 |
| 6,488,651 | B1 * | 12/2002 | Morris .............. A61M 5/31596 |
| | | | 604/89 |
| 6,547,432 | B2 * | 4/2003 | Coffeen ............. A61B 17/8822 |
| | | | 366/130 |
| 6,571,992 | B2 * | 6/2003 | Pierson ............. B65D 83/0011 |
| | | | 222/390 |
| 8,394,105 | B2 * | 3/2013 | Vendrely ........... A61B 17/8833 |
| | | | 606/92 |
| 2004/0020811 | A1 | 2/2004 | Yamanaka |
| 2011/0125088 | A1 * | 5/2011 | Dixon ................ A61B 17/8822 |
| | | | 604/82 |
| 2012/0244493 | A1 * | 9/2012 | Leiner .................... A61C 5/062 |
| | | | 433/90 |
| 2016/0022917 | A1 * | 1/2016 | Takai ................ A61M 5/31513 |
| | | | 604/222 |

* cited by examiner

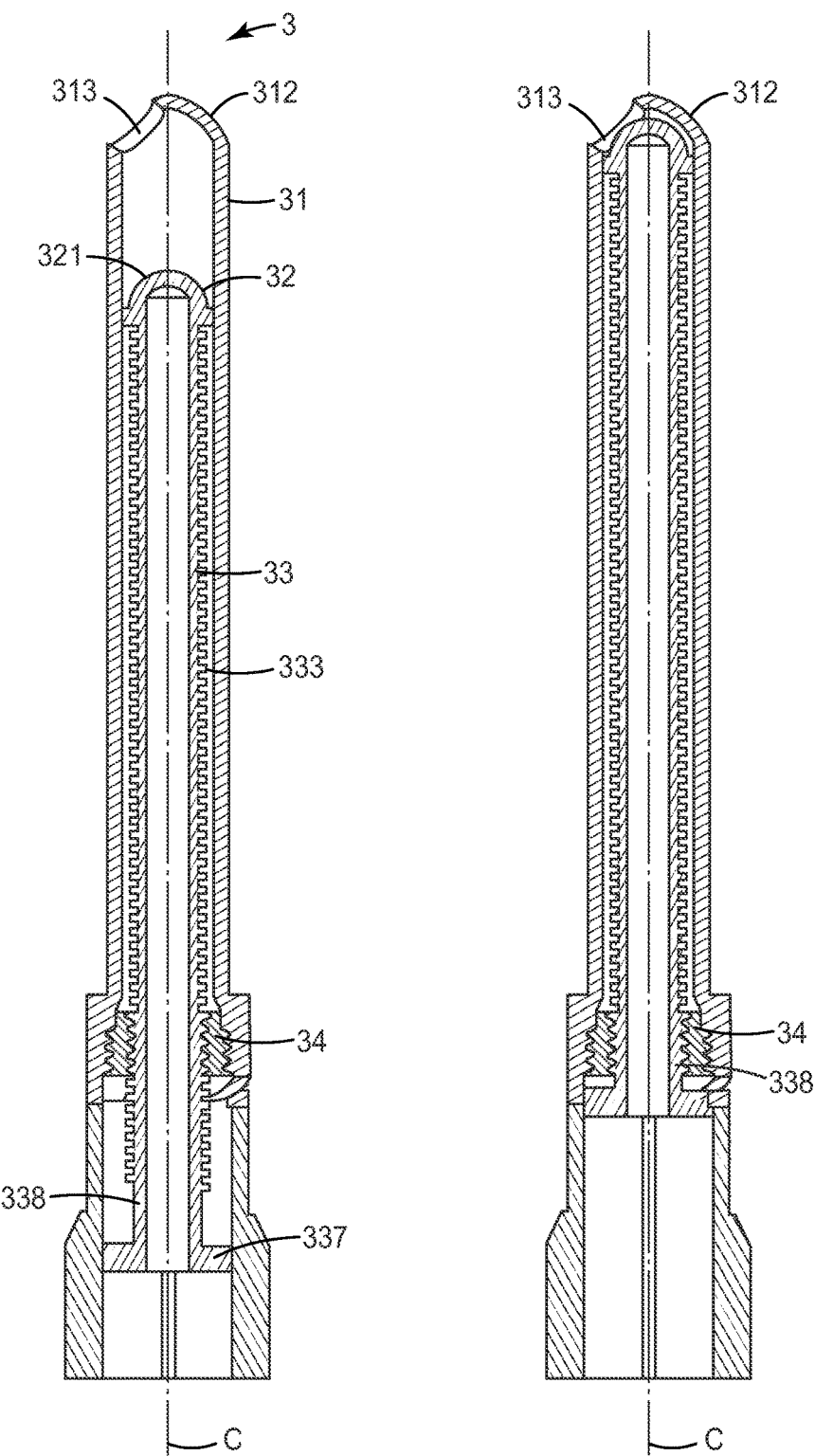

DEVICE FOR DISPENSING A MATERIAL

FIELD OF THE INVENTION

The invention relates to a device for dispensing a material, and in particular to a device having a piston and a spindle which in one operation mode of the device are rotatable relative to each other so that rotating the spindle does not necessarily rotate the piston, and which in a further operation mode of the device the spindle and the piston are anti-twist locked with each other so that rotating the spindle also causes the piston to rotate.

BACKGROUND ART

Many dental materials exhibit a relative high viscosity and therefore are provided in so-called screw syringes. Such a syringe is for example disclosed in U.S. Design Pat. No. Des. 419,236.

Further WO 2006/108085 A2 discloses a syringe delivery system for dispensing a highly viscous material through a syringe delivery opening. The system includes a syringe barrel having a delivery opening, a plunger including a threaded shaft that threadably engages the syringe barrel for selectively dispensing a viscous material through the delivery opening, and a plunger gripping member in gripping communication with the plunger that includes means for sealing the threaded shaft of the plunger so as to prevent contamination by foreign matter.

Although a variety of useful syringes for dental filling materials are available it has been found that there is a desire from users of such syringes to use substantially all of the material stored in a syringe. Further such a syringe is desirably easy to use and relatively inexpensive.

SUMMARY OF THE INVENTION

The invention in a first aspect relates to a device for dispensing a material, preferably a dental material. The device comprises a container for holding or storing the material. The device further comprises a piston movably arranged within the container and a spindle in cooperation with the piston. The device is configured such that the spindle and the container are rotatable about a rotation axis relative to each other to (axially) move the piston for dispensing the material. The piston and the spindle are adapted to anti-twist lock against each other in a first axial position of the piston relative to spindle, whereas in a second axial position of the piston relative to spindle the anti-twist lock between the piston and the spindle is suspended. The first axial position and the second axial position refer to two different positions of the piston and the spindle relative to each other in a dimension of the rotation axis.

The invention is advantageous in that it helps minimizing any residual amount of dental material in the device upon attempts to empty the device. Further the invention helps a user recognizing when the device is empty and no further material is container therein.

In an embodiment the spindle and the container are (directly or indirectly) threadably engaged with one another. The thread engagement is preferably such that—in the second axial position of the piston and the spindle—a rotation of the spindle and the container relative to each other causes the spindle to move axially relative to the container. Further the device is preferably adapted such that an axial movement of the spindle relative to the container also causes the piston to move axially relative to the container. A device implementing an indirect threaded engagement may comprise a nut that is axially and rotationally fixed with the container and which forms an inner thread being in engagement with an outer thread of the spindle. The nut may for example be press fit, welded or glued into the container. A device implementing a direct threaded engagement may comprise a container forming itself an inner thread being in engagement with an outer thread of the spindle.

In an embodiment a front end of the spindle is located inside the container and an opposite rear end of the spindle is located outside the container. The front end of the spindle may comprise in a direction of the spindle front end toward the spindle rear end a first section, a second section and a third section consecutively arranged in the order as listed. The piston preferably has a front end and a rear end with a receptacle extending from the rear end into the piston. The receptacle is preferably formed by a blind-hole into the piston. The receptacle preferably has a first section adjacent the piston rear end and a second section further toward the piston front end. In the first axial position of the piston and the spindle preferably the piston second section is engaged with the spindle first section, and in the second axial position of the piston and the spindle the piston second section and the spindle first section are disengaged from each other.

Further in the first axial position of the piston and the spindle the piston first section may be further mated with both, the spindle second and third section, whereas in the second axial position of the piston and the spindle the piston first section may be mated with the spindle second section but not with the spindle third section.

In a further embodiment the piston second section and the spindle first section are shaped such that in a situation in which the piston second section and the spindle first section are mated they form an anti-twist lock (with respect to a rotation of the spindle and the piston about the rotation axis) for the piston and the spindle relative to each other. Such a shape may comprise a non-cylindrical shape of the piston second section and the spindle first section and/or a structure of the piston second section and the spindle first section being located in an off-center relationship to the rotation axis, for example. The piston first section and the spindle second section may be adapted to form a rotatable fit with each other, for a rotation of the piston and the spindle relative to each other. Further the piston first section and the spindle third section may be adapted to form a press fit with each other. The piston first section and the spindle third section are preferably adapted such that mating requires a certain minimum force or threshold force. The piston is preferably received with its receptacle on the front end of the spindle.

In one embodiment the spindle is received axially stationary but rotatable within the container. In the second axial position of the piston and the spindle the piston and the spindle may be threadably engaged with each other and the piston and the container are retained against rotation relative to each other. Thus in the second axial position of the piston and the spindle a rotation of the spindle and the container relative to each other causes the piston to move axially relative to the container.

In a further embodiment the spindle and the piston are (directly or indirectly) threadably engaged with one another, at least in the second axial position of the piston and the spindle. Thus a rotation of the spindle and the piston relative to each other causes the piston to move axially relative to the container.

In an embodiment the spindle has a front end being located inside the container and an opposite rear end located outside the container. The spindle preferably comprises an engagement structure adjacent the front end and an outer thread that may extend between the front and the rear end. The piston preferably has a front end and a rear end and a through-hole extending between the piston front and rear end. The through-hole may form or comprise an inner thread for engagement with the spindle outer thread. Further the piston may have an engagement structure adjacent the piston front end. In the first axial position of the piston and the spindle the engagement structures of the spindle and the piston are preferably engaged with one another, and in the second axial position of the piston and the spindle the engagement structures of the piston and the spindle are preferably disengaged from each other.

In a further embodiment the piston is press fit with the container. Thus a good seal between the piston and the container may be achieved.

In one embodiment in the second axial position of the piston and the spindle a volume for the material is formed between the container and the piston, whereas in the first axial position such volume is eliminated. The container preferably has a front end and an opposite rear end and the spindle preferably extends into the container rear end. Further the container preferably has an outlet for the material at the front end. The device may comprise the dental material, in particular a dental composite filling material.

In a further embodiment the device comprises a cap received on the front end of the container. The cap preferably has an aperture. The container and the cap may be configured to form a valve with each other being operable between an open position and a closed position. In the open position the aperture of the cap and the outlet of the container overlap, whereas in the closed position a wall of the cap seals or closes the outlet of the container.

The device of the invention may be filled with a dental material, particularly a dental filling material.

In a second aspect the present invention relates to a device for dispensing a material, for example a dental material and particularly a dental filling material. The device comprises a container for holding the material, a piston movably arranged within the container and a spindle in cooperation with the piston. The spindle has a front end adjacent the piston and an opposite rear end. The device is configured such that the spindle and the container are rotatable about a rotation axis relative to each other to move the piston for dispensing the material. The spindle and the container are positionable in a first axial position and a second axial position. In the second axial position the spindle and the container are threadably connected with each other so that a rotation of the spindle and the container relative to each other causes the spindle and the container to axially move relative to each other. In the first axial position the threaded connection between the spindle and the container is suspended so that a rotation of the spindle and the container relative to each other is enabled without causing the spindle and the container to axially move relative to each other. The first and second axial position refer to two different positions in a dimension of the rotation axis. The spindle has an outer thread and a groove adjacent the rear end of the spindle. The groove is dimensioned smaller in diameter than the minor thread diameter of the outer thread. In the second axial position the thread of the nut and the outer thread of the spindle are engaged, whereas in the first axial position the thread of the nut cooperates with the groove of the spindle so that the threaded connection between the spindle and the container is suspended.

In the embodiment of the second aspect the piston and the spindle may in combination form one integral or monolithic part. The embodiment of the second aspect is advantageous in that it helps minimizing any residual amount of dental material in the device upon attempts to empty the device. Further the embodiment helps a user recognizing when the device is empty and no further material is container therein.

The device of the second aspect may comprise a threaded nut, in particular a nut having an inner thread being in engagement with an outer thread of the spindle in the second axial position. The nut may be attached or fixedly connected with the container, for example press fit, welded or glued.

Further the container of the device of the second aspect may have an outlet for the material at the front end. The device may comprise the dental material, in particular a dental composite filling material. The device may comprise a cap received on the front end of the container. The cap preferably has an aperture. The container and the cap may be configured to form a valve with each other being operable between an open position and a closed position. In the open position the aperture of the cap and the outlet of the container overlap, whereas in the closed position a wall of the cap seals or closes the outlet of the container.

BRIEF DESCRIPTION OF THE FIGURES

FIG. 7 is a cross-sectional view of a device according to an embodiment of the second aspect of the invention; and FIG. 8 is a cross-sectional view of the device of FIG. 7 at a different stage of operation.

DETAILED DESCRIPTION OF THE INVENTION

Figure 1:
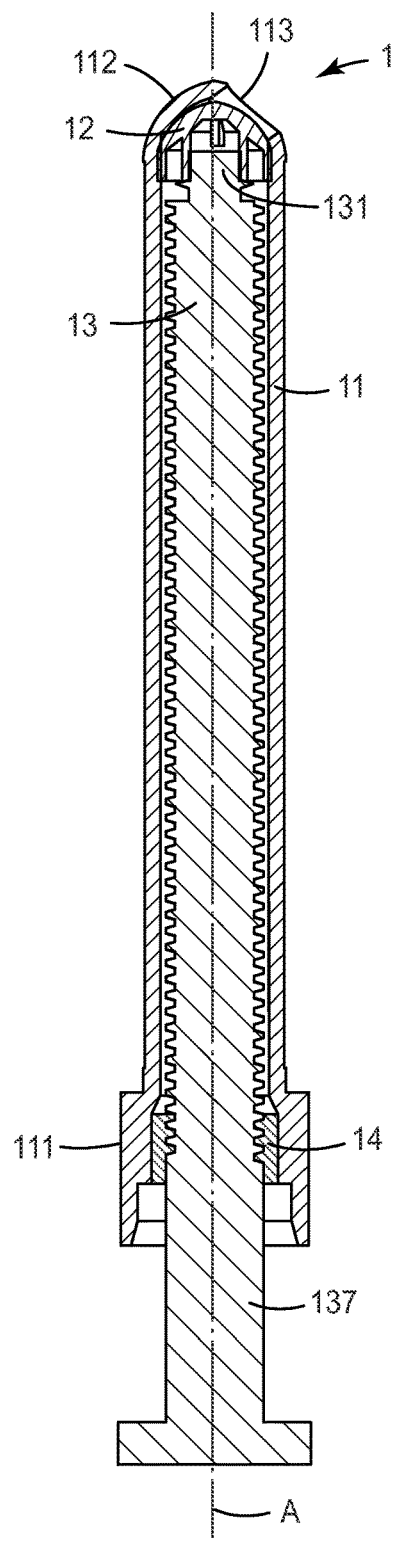
FIG. 1 is a cross-sectional view of a device according to an embodiment of the invention.

FIG. 1 shows a device 1 for dispensing a dental material according to one embodiment of the invention. The device has a container 11 for holding the dental material. A piston 12 is arranged movably within the container 11. Further the device 1 has a spindle 13 arranged for cooperation with the piston 12. In particular the piston 12 is received on a front end 131 of the spindle 13. The spindle 13 and the container 11 are connected by a threaded connection with each other and rotatable about a rotation axis A relative to each other. Therefore by rotating the spindle 13 and the container 11 relative to each other the spindle 13 and the container 11 move axially relative to each other. Thus by rotating the spindle 13 and the container 11 in a first direction relative to each other the piston 12 can be urged into the container 11 for dispensing the material. The device 1 may have a reverse lock (not shown) which prevents the spindle 13 and the container 11 from being rotated in an opposite second direction. Thus the piston 12 may be prevented from being retracted. This may for example avoid air to be pulled into the device 1 which may help maximizing the shelf life of material remaining in the device 1.

Figure 2:
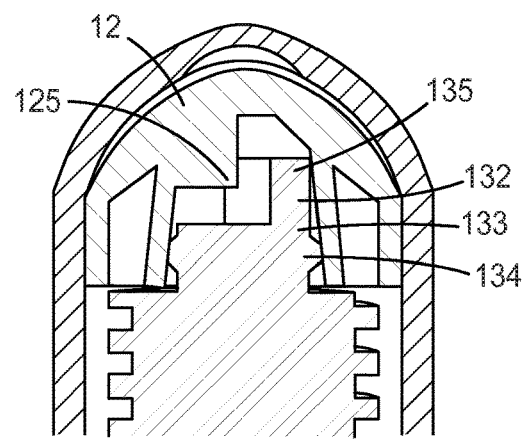
FIG. 2 is an enlarged view a detail of the device shown in FIG. 1 at a first stage of operation.

The piston 12 and the spindle 13 are adapted for optionally anti-twist locking against each other. FIG. 2 shows the piston 12 and the spindle 13 in a first axial position relative to each other. In the first axial position an engagement structure 135 of the spindle 13 engages with an engagement structure 125 of the piston 12 so that the piston 12 and the spindle 13 are rotationally locked with each other. In the example the spindle engagement structure 135 is formed by a protrusion extending generally parallel to the rotation axis A but which is arranged in an off-center relationship with the rotation axis A. The protrusion engages a blind hole in the piston 12 which also extends into the piston 12 generally parallel to the rotation axis A and which is arranged in an off-center relationship with the rotation axis A.

Figure 3:
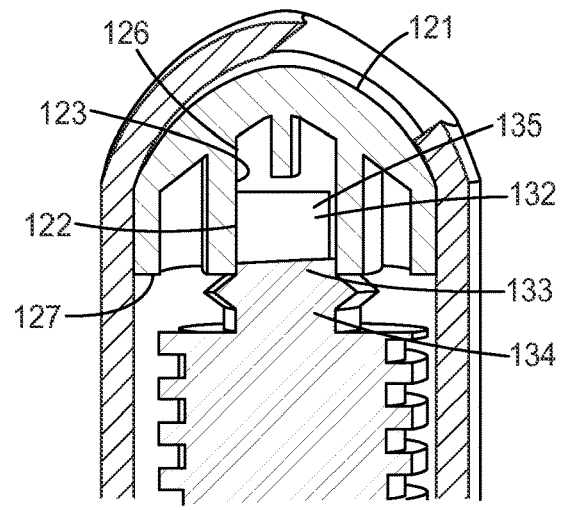
FIG. 3 is an enlarged view a detail of the device shown in FIG. 1 at a second stage of operation.

In a second axial position of the piston 12 relative to spindle 13 the anti-twist lock between the piston 12 and the spindle 13 is suspended as illustrated in FIG. 3. In the second axial position the spindle engagement structure 135 is disengaged from the piston engagement structure 125 so that the piston 12 and the spindle 13 can rotate relative to each other. Therefore depending on whether the piston 12 and the spindle 13 are positioned in the first or second axial position the piston 12 and the spindle 13 are rotationally locked or rotatable relative to each other, respectively.

The second axial position of the piston 12 and the spindle as shown in FIG. 3 is preferably established during dispensing the dental material. Accordingly the spindle 13 may be rotated relative to the container 11 so that the spindle 13 is screwed into the container 11, thereby pushing the piston 12 forward for dispensing the dental material. Because in the second axial position the piston 12 and the spindle 13 are rotatable relative to each other the piston 12, preferably being press fit in the container 11 for tight sealing, does not rotate relative to the container 11. Thus the force for rotating the spindle 13 and the container 11 relative to each other may be minimized relative to a configuration in which the piston is not rotatable relative to the spindle. Preferably the second axial position of the piston 12 and the spindle 13 is initially established in a situation in which the container is full of dental material, meaning at a stage at which still nothing of the dental material contained in the device 1 has been dispensed therefrom. This may be provided by the manufacturer of the device 1, for example. The device is adapted such that the piston 12 and the spindle 13 remain in the second axial position as long as an axial force urging the piston 11 and the spindle 13 toward each other are within a range of 0 N to about a threshold force of 1000 N, more preferably within a range of 0 N to about a threshold force of 500 N, and most preferably within a range of 0 N to about a threshold force of 200 N. The device 1 is further adapted such that, upon exceeding the threshold force, the piston 11 and the spindle 13 move into the first axial position.

In more particular the spindle front end 131 comprises a first section 132, a second section 133 and a third section 134, and the piston 12 comprises a receptacle 126 having a first section 122 and a second section 123. The spindle first, second and third section 132, 133, 134 are arranged with the spindle first section 132 arranged adjacent the spindle front end 131, the spindle third section 134 further toward a rear end 137 of the spindle 13, and with the spindle second section 133 arranged between the spindle first and third section 132, 134. Preferably the spindle first, second and third section 132, 133, 134 are arranged directly adjacent each other without a space or other section arranged between. Further the piston has a front end 121 and a rear end 127, and the receptacle 126 extends from the piston rear end 127 into the piston 12 in a direction toward the piston front end 121. The piston first section 122 is arranged adjacent the piston rear end 127 and the piston second section 123 is arranged further toward the piston front end. Preferably the piston first section 123 and the piston second section 123 are arranged directly adjacent each other without a space or other section arranged between.

In the example the spindle first section 132 comprises the spindle engagement structure 135. Further the spindle second section 133 is formed by a generally cylindrical portion of the spindle 13, and the spindle third section 134 is formed by a bulge or rim of a greater diameter than the cylindrical portion of the spindle second section 133.

Further in the example the piston first section 122 is formed by a generally cylindrical portion of the receptacle 126 of the piston 12, whereas the piston second section 123 comprises the engagement structure 125.

Accordingly in the first axial position of the piston 12 and the spindle 13 the piston second section 123 is engaged with the spindle first section 132, and in the second axial position of the piston 12 and the spindle 13 the piston second section 123 and the spindle first section 132 are disengaged from each other.

As illustrated in FIG. 1 the spindle 13 is located with its front end 131 inside the container and the spindle rear end 137 outside the container 11. A threaded nut 14 may be fixed within the container 11 and a rear end 111 of the container 11. For example the threaded nut 14 may be press fit and/or glued into the container 11. Instead of or in addition to gluing the threaded nut 14 may be welded, snap fit, or screwed with the container. Other connections may be used as appropriate.

Further the container 11 has preferably at its front end 112 has a dispensing outlet 113 for the dental material. Therefore in operation of the device 1 the spindle 13 and the container 11 may be rotated relative to each other for dispensing the dental material from the device 1. As the piston 12 approaches the front end 112 of the container 11 a further operation of the device 1 to dispense material causes the piston 12 to be pressurized between the spindle 13 and consequently an axial force urging the piston 12 and the spindle 13 toward one another to increase. Thus upon exceeding the threshold axial force the piston 12 and the spindle 13 move from the second to the first axial position. In the first axial position a further rotation of the spindle 13 and the container 11 relative to each other causes the piston 12 to also rotate. Therefore any material between the piston front end 121 and the inner container front end 112 is striped off in the area of the outlet 113 as the piston 12 rotates relative to the outlet 113. Thus the device 1 is advantageous in that it can be substantially entirely emptied.

Figure 4:
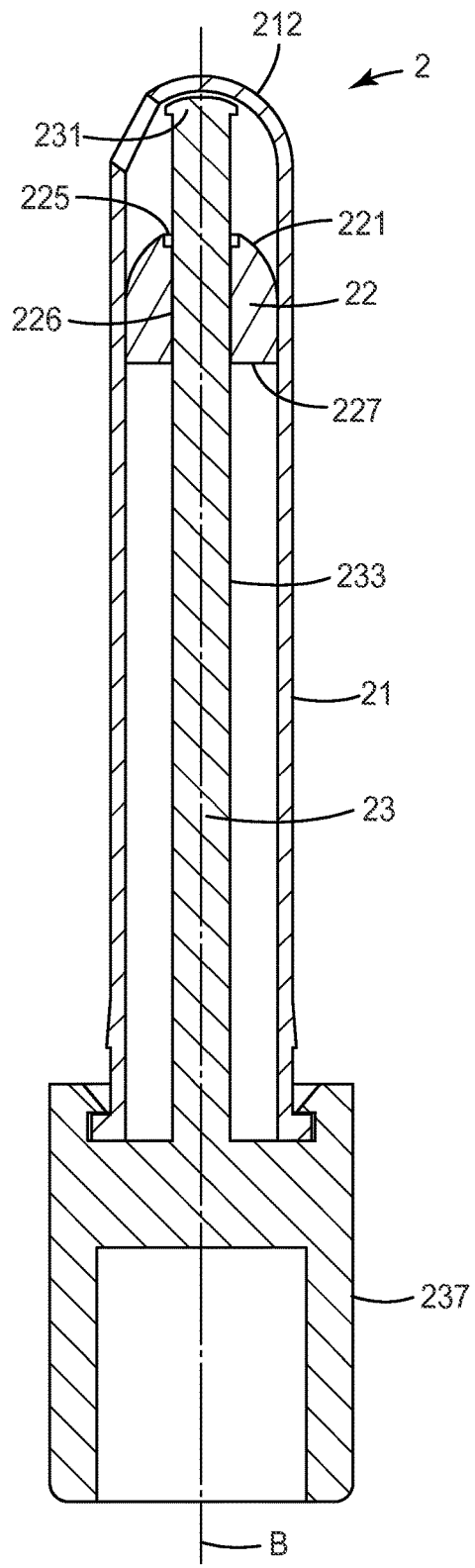
FIG. 4 is a cross-sectional view of a device according to a further embodiment of the invention.

FIG. 4 shows a device 2 according to a further embodiment of the invention. The device 2 has a container 21 for holding a dental material. A piston 22 is movably arranged within the container 21. A spindle 23 is arranged within the device 2 for cooperation with the piston 22. In particular the piston 22 is received on the spindle 23. In this embodiment the spindle 23 and the container 21 are arranged axially stationary but rotatable relative to each other. The spindle 23 has a front end 231 having an engagement structure 235 adjacent the front end 231 and an outer thread 233 between the front end 231 and a rear end 237 of the spindle 23. Further the piston 22 has a front end 221 and a rear end 227 and a through-hole 226 extending between the front end 221 and the rear end 227. The piston 22 forms within the through-hole 226 an inner thread for engagement with the outer thread 233 of the spindle 23. The piston 22 has further an engagement structure 225 adjacent the front end 221 of the piston 22.

Figure 5:
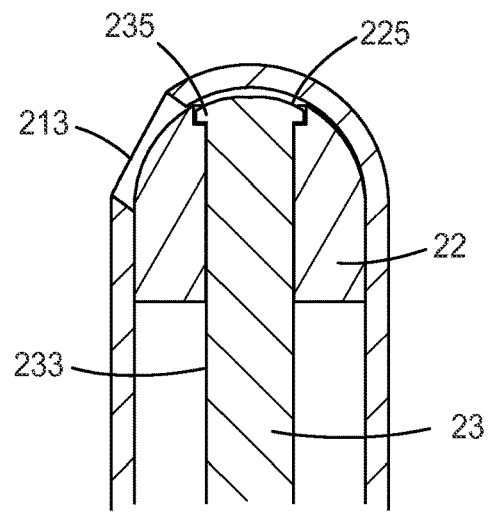
FIG. 5 is an enlarged view a detail of the device shown in FIG. 4 at a first stage of operation.
Figure 6:
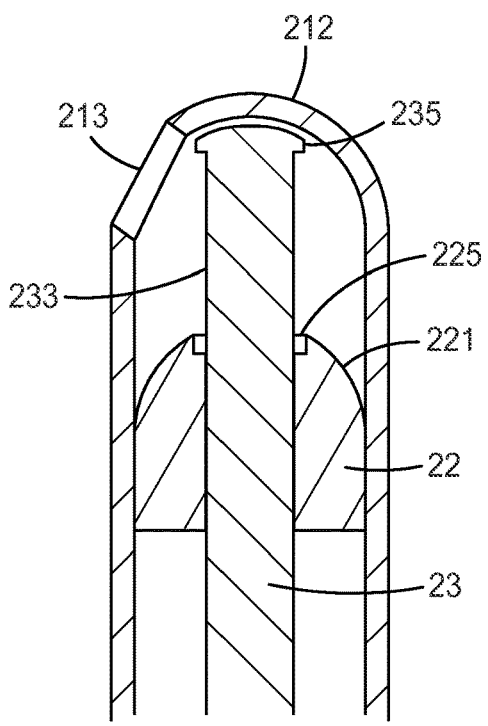
FIG. 6 is an enlarged view a detail of the device shown in FIG. 4 at a second stage of operation.

The piston 22 and the spindle 23 are adapted for optionally anti-twist locking against each other. As illustrated in FIG. 5 in a first axial position of the piston 22 and the spindle 23 the engagement structures 235, 225 of the spindle 23 and the piston 22 are engaged with one another, and in a second axial position, as shown in FIG. 6, the engagement structures 235, 225 of the spindle 23 and the piston 22 are disengaged from each other. Thus in the first axial position the engagement structure 235 of the spindle 23 engages with the engagement structure 225 of the piston 22 so that the piston 22 and the spindle 23 are rotationally locked with each other. In the example the spindle engagement structure 235 is a non-cylindrical structure which outer periphery protrudes over an outer diameter of the spindle thread 233. In the example the non-cylindrical structure is formed by a web which protrudes form the spindle 23 in a dimension laterally of the rotation axis B. In the second axial position of the spindle 23 and the piston 22 are rotatable such that spindle 23 and the piston 22 can be screwed with one another. Accordingly in the second axial position the spindle 23 and the piston 22 can be rotated relative to each other for dispensing the dental material. The piston 22 is preferably press fit within the container 21. Thus a tight seal between the container 21 and the piston is formed. Further due to the press fit the piston 22 and the container 21 are rotationally retained relative to each other, preferably due friction forces. Therefore a rotation of the spindle 23 relative to the container 21 normally causes also a rotation of the spindle 23 relative to the piston 22. Hence the dental material can be dispensed by a rotation of the spindle 23 relative to the container 21 in the second axial position of the spindle 23 and the piston 22.

The container 21 has at its front end 212 has a dispensing outlet 213 for the dental material. Therefore in operation of the device 2 the spindle 23 and the container 21 may be rotated relative to each other for dispensing the dental material from the device 2. Further the spindle 23 is located inside the container 21 and the spindle rear end 227 is located outside the container. The spindle 23 has a length so that the spindle front end 231 is located adjacent the container front end 212. Accordingly in operation of the device for dispensing material, once the piston 22 has reached the front end 231 of the spindle 23 the engagement structure 235, 225 of the spindle 23 and the piston 22, respectively, engage with each other so that the first axial position is established. In the first axial position of the spindle 23 and the piston 22 a further rotation of the spindle 23 relative to the container 21 also causes the piston 22 and the container to rotate relative to each other. Therefore any material between the piston front end 221 and the inner container front end 212 is striped off in the area of the outlet 213. This is because the piston 22 rotates relative to the outlet 213. The device 2 is therefore advantageous in that it can be substantially entirely emptied.

FIG. 7 shows a device 3 according to the second aspect of the invention. The device 3 has a container 31 for holding a dental material. A piston 32 is movably arranged within the container 31. In this embodiment the piston 32 is integral part of a spindle 33. The spindle 33 and the container 31 are connected by a threaded connection with each other and rotatable about a rotation axis C relative to each other. The threaded connection between the spindle 33 and the container 31 is configured for disengaging in a first axial position of the spindle relative to the container 31, whereas in a second axial position the threaded connection is in engagement. In the first axial position a piston front end 321 is in contact or close proximity to a front end 312 of the container (illustrated in FIG. 8). Thus any space between the piston 32 and the container 31 is substantially eliminated so that substantially all material initially contained in the container 31 is displaced therefrom.

In the second axial position rotating the spindle 33 and the container 31 relative to each other causes the spindle 33 and the container 31 to move axially relative to each other. In the second axial position the piston 32 and the container 31 are spaced and that space is preferably filled with the dental material. Therefore in the second position rotating the spindle 33 and the container 31 in a first direction relative to each other causes the piston 32 to be urged into the container 31 such that the space is reduced and the material is caused to be dispensed. Once the spindle 33 and the container 31 reach the first axial position the threaded connection disengages. In the example the spindle 33 has an outer thread 333 and a groove 338 adjacent a rear end 337 of the spindle 33. The groove 338 is dimensioned smaller in diameter than the minor thread diameter of the outer thread 333. Further a threaded nut 34 is attached to the container 31. In the second axial position of the spindle 33 and the container 31 the thread of the nut 34 and the outer thread 333 of the spindle 33 are engaged, whereas in the first axial position of the spindle 33 and the container 31 the thread of the nut 34 cooperates with the groove 338 of the spindle 33 so that the threaded connection between the spindle 33 and the container 31 is suspended. Therefore in the first axial position the spindle 33 and the container 31 can be rotated relative to each other without causing any (further) axial movement between the spindle 33 and the container 31.

In operation of the device 3 the spindle 33 and the container 31 may be rotated relative to each other for dispensing the dental material from the device 3. As the piston 32 approaches the front end 312 of the container 31 a further operation of the device 3 to dispense material causes the spindle 33 and the container 31 to reach the first axial position and the threaded connection between the spindle 33 and the container 31 to disengage. In the first axial position a further rotation of the spindle 33 and the container 31 relative to each other causes the piston 32 to rotate without axial further movement. Therefore any material between the piston front end 321 and the inner container front end 312 is striped off in the area of an outlet 313 as the piston 32 rotates relative to the outlet 313. Thus the device 3 is advantageous in that it can be substantially entirely emptied.

The invention claimed is:

1. A device for dispensing a material, the device comprising:
   a container for holding the material;
   a piston movably arranged within the container, wherein the piston has a front end and a rear end with a receptacle extending from the rear end into the piston, the receptacle having a piston first section adjacent the piston rear end and a piston second section further toward the piston front end, the piston second section being located in an off-center relationship to a rotation axis; and
   a spindle in cooperation with the piston, wherein the device is configured such that the spindle and the container are rotatable about the rotation axis relative to each other to move the piston for dispensing the material, wherein a front end of the spindle is located inside the container and a rear end of the spindle is located outside the container, the front end comprising a spindle first section, a spindle second section and a spindle third section consecutively arranged in a direction of the front end toward the rear end, the spindle first section being located in an off-center relationship to the rotation axis and wherein the piston and the spindle are adapted to anti-twist lock against each other in a second axial position of the piston relative to the spindle in which the piston second section is engaged with the spindle first section, wherein in a first axial position of the piston relative to the spindle the piston second section is disengaged from the spindle second section such that the anti-twist lock between the piston and the spindle is suspended, with the first and second axial position referring to two different positions in a dimension of the rotation axis, and wherein the piston and the spindle are adapted to move to the second axial position of the piston relative to the spindle after being in the first axial position.

2. The device of claim 1, wherein the spindle and the container are threadably engaged with one another such that a rotation of the spindle and the container relative to each other causes the spindle to move axially relative to the container.

3. The device of claim 2, further comprising a nut having an inner thread being in engagement with an outer thread of the spindle, wherein the nut is fixedly connected with the container.

4. The device of claim 1, wherein in the second axial position of the piston relative to the spindle, the piston first section is further mated with the spindle second section and the spindle third section, whereas in the first axial position of the piston relative to the spindle, the piston first section is mated with the spindle second section but not with the spindle third section.

5. The device of claim 1, wherein the piston second section and the spindle first section are shaped such that in a situation in which the piston second section and the spindle first section are mated they form an anti-twist lock for the piston and the spindle relative to each other.

6. The device of claim 1, wherein the piston first section and the spindle second section are adapted to form a rotatable fit with each other, for a rotation of the piston and the spindle relative to each other.

7. The device of claim 1, wherein the piston first section and the spindle third section are adapted to form a press fit with each other.

8. The device of claim 1, in which the piston is received with the receptacle on the front end of the spindle.

9. The device of claim 1, wherein the piston second section is formed by a blind-hole into the piston.

* * * * *